Figure 1:
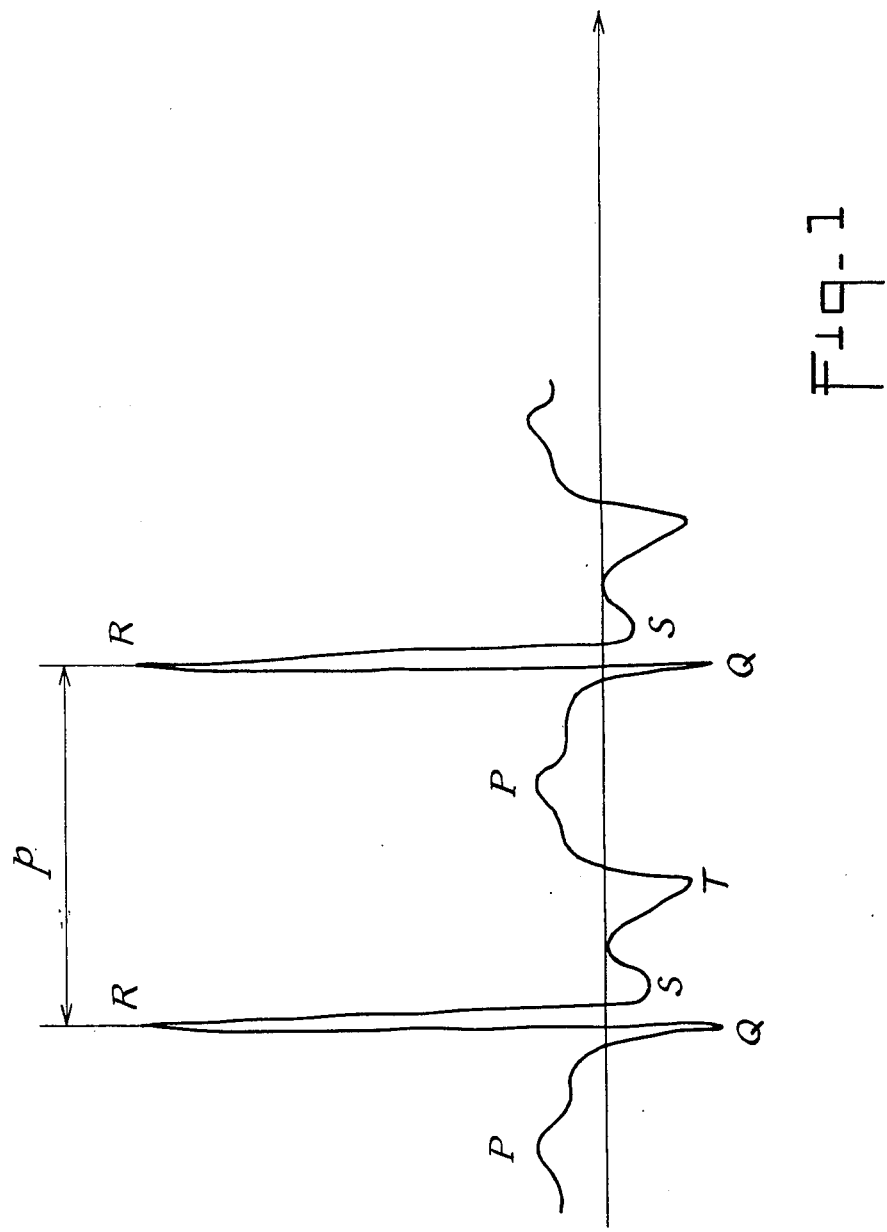

United States Patent [19]

Faisandier

[11] 4,275,742
[45] Jun. 30, 1981

[54] PROCESS AND DEVICE FOR PROCESSING AND DISPLAYING A READ-OUT SIGNAL FROM AN ELECTROCARDIOGRAM RECORDING READ AT A SPEED GREATER THAN THE SPEED OF RECORDING

[75] Inventor: Yves Faisandier, Paris, France

[73] Assignee: C.M. Industries, Paris, France

[21] Appl. No.: 36,986

[22] Filed: May 8, 1979

[30] Foreign Application Priority Data

May 12, 1978 [FR] France .................................. 78 14293

[51] Int. Cl.³ ............................................... A61B 5/04
[52] U.S. Cl. .................................... 128/703; 128/704
[58] Field of Search ............... 128/702, 703, 704, 706, 128/709, 710, 711, 700

[56] References Cited
U.S. PATENT DOCUMENTS 3,616,790  11/1971  Harris ................................... 128/702
3,658,055  4/1972   Abe et al. ............................. 128/703
3,853,119  12/1974  Peterson et al. ..................... 128/711
3,940,692  2/1976   Neilson ................................ 128/702
4,022,192  5/1977   Laukien ............................... 128/706
4,181,135  1/1980   Andresen et al. .................... 128/703

Primary Examiner—William E. Kamm
Attorney, Agent, or Firm—Lewis H. Eslinger

[57] ABSTRACT

A process and device for processing and displaying an electrocardiogram signal read at a speed greater than the speed of recording, in which process a plurality of types of pathological complexes are selectively and simultaneously detected with the aid of discriminators on the signal read, and on each of a plurality of distinct display locations there is displayed each signal sequence presenting a complex of a type corresponding to said display location. The process and device are more particularly applicable to the statistical processing such as the drawing up of a histogram of the pathological occurrences of an electrocardiogram signal.

9 Claims, 2 Drawing Figures

PROCESS AND DEVICE FOR PROCESSING AND DISPLAYING A READ-OUT SIGNAL FROM AN ELECTROCARDIOGRAM RECORDING READ AT A SPEED GREATER THAN THE SPEED OF RECORDING

The present invention relates to a process and a device for processing and displaying a read-out signal from an electrocardiogram recording read at a speed greater than the speed of recording.

An electrocardiogram is known to be a periodic curve of which each cycle or pattern normally presents three waves referenced by the letters P, QRS and T (FIG. 1).

The so-called HOLTER investigation process consists in effecting on a patient a continuous electrocardiogram recording over a long period, for example over 24 hours. This recording is made on the magnetic tape of a cassette.

It is a particular object of the invention to propose a process and a device allowing a rapid and efficient utilization of this electrocardiogram recording with a view to establishing an accurate and reliable diagnosis.

To this end, the process for processing an electrocardiogram signal recorded over a long period and read at a speed at least ten times greater than the speed of recording, is characterised, according to the invention, by the selective and simultaneous detection of a plurality of different types of pathological complexes on the signal read, and the display on each of a plurality of distinct display locations, of each signal sequence presenting the complex of a type corresponding to said display location.

A determined type of pathological complex is advantageously detected selectively by measuring each period or duration of cycle of the electrocardiogram signal and/or by measuring the mean value of n consecutive periods, n being an integer greater than 1, and/or by comparing this period or this mean value with a reference value, and by detecting each period or mean value lower or higher than this reference value, and/or by detecting each series of p consecutive cycles of which the periods are lower—or higher—than this reference value, and/or by comparing the period or the mean value with two reference values and by detecting each period of which the value is included—or not included—between these two reference values, and/or by calculating each difference between one period and the immediately preceding period and by comparing this difference with a reference value.

A pathological complex may also be detected by comparing the shape of each cycle with a reference shape by a shape recognition method.

This process is advantageously carried out in a device which comprises:
a magnetic tape reader;
a device introducing a delay in the signal furnished by the reader;
a plurality of main memories each receiving the signal coming from the delay device;
discriminators each associated with a main memory and each receiving the non-delayed signal from the reader;
a display apparatus comprising a plurality of distinct display locations of which each is associated with a main memory for displaying the contents of this memory; each discriminator being arranged to recognize a pathological complex of corresponding type and to send to the memory with which it is associated, an order to record a sequence of the signal of the delay device whereby there is associated with each display location a particular type of pathological complex and each pathological complex of a type detected by a discriminator is displayed on the corresponding display location.

Thus, the selective display of certain, suitably chosen types of pathological complexes allows a rapid investigation of the electrocardiogram recording.

Moreover, this process allows the drawing up of exact statistics, allowing the operator to visually examine each cycle detected as pathological by the device.

Figure 2:
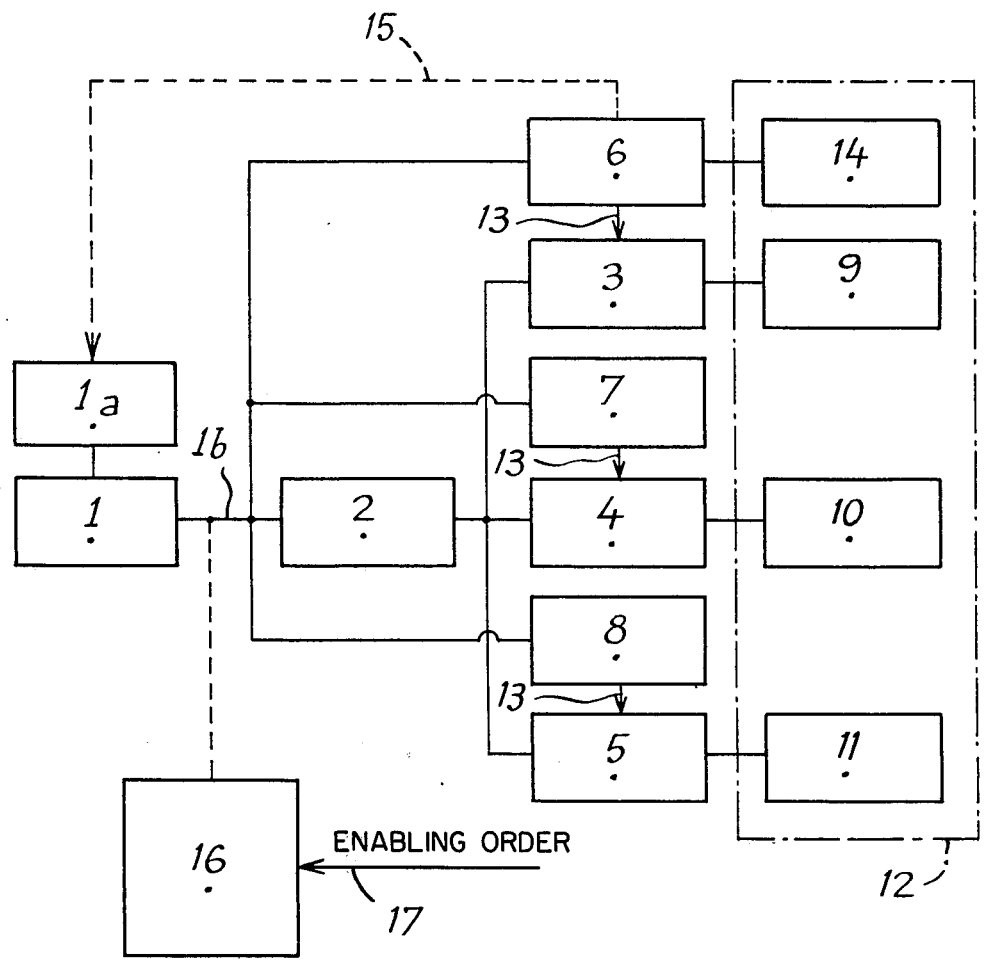

The invention will be more readily understood on reading the following description with reference to the accompanying drawings, in which:

FIG. 1 is an electrocardiogram tracing, and
FIG. 2 is a diagram of a processing and display device according to an embodiment of the invention.

The device shown is designed selectively and simultaneously to detect a plurality, for example three different types of pathological complexes appearing in an electrocardiogram recorded over a long period, for example over 24 hours, on a patient; this device makes it possible to display, simultaneously and on different parts of the screen, the sequences comprising these complexes, each screen part being associated with a particular type of complex.

To this end, a cassette comprising an electrocardiogram recording on magnetic tape made over a long period of time, is read at high speed in a cassette reader 1 of which the motor 1a drives the tape at a speed about 100 times faster than the speed of recording of this tape.

The output signal 1b of the reader 1 is applied, after having been delayed in a delay device 2, on three main memories 3,4,5 simultaneously; this signal is also applied, but without being delayed, on three discriminators 6,7,8 simultaneously. Each discriminator 6,7,8 is associated with a main memory 3,4,5 respectively, of which the contents are observed on a channel 9,10, 11 respectively of a display apparatus 12; the function of each discriminator 6,7,8 is to recognize a particular type of pathological complex.

When a discriminator 6,7,8 detects the type of pathological complex with which it is associated, it gives the memory 3,4,5 with which it is associated an order 13 for recording a sequence of the signal coming from the delay device 2. Three sequences of the readout signal of the cassette are thus obtained simultaneously on the screen of the display apparatus 12, each sequence appearing on a particular part of the screen, said part corresponding to the channel 9, 10, 11 associated therewith, each sequence—or sample of signal—comprising a pathological complex of the particular type associated with said part of the screen.

The display apparatus 12 allows the display of sequences of length corresponding to a duration of readout t of the reader 1; the capacity of each memory 3,4,5 is equal to the data content of such a length of sequence and the delay device 2 introduces in the signal coming from the reader 1 a delay t/2; this results in the pathological complex detected by a discriminator 6,7,8 and displayed on the screen of the apparatus 12 being located in the middle of the sequence displayed on this screen.

According to a preferred embodiment of the invention, a first display channel 9 is reserved for the samples in which a considerable variation is detected between two consecutive periods $p_i$ of the electrocardiogram signal 1b; a second channel 10 is reserved for the samples in which either a period $p_i$ corresponding to an actual electrocardiogram period greater than two seconds is detected, or a pause, i.e. an absence of signal, of actual duration greater than 2 seconds; a third channel 11 is reserved for the samples in which a rhythm is detected, corresponding to an actual rhythm greater than 150 patterns per minute or less than 45 patterns per minute; and a fourth channel 14 displays the curve of the value of the periods $p_i$ as a function of time.

To these ends, the discriminator 6 measures each period $p_i$ of the signal by using the consecutive signals QRS, calculates $\Delta_p = |p_i - p_{i-1}|$, compares $\Delta_p$ with a reference threshold value and transmits an order 13 to the memory 3 as soon as $\Delta_p$ exceeds this threshold; the discriminator 7 also measures each period $p_i$ and applies an order 13 to the memory 4 as soon as $p_i > 2$ secs.; the discriminator 8 measures each period $p_i$, calculates the mean value of n consecutive $p_i$'s, n being an integer greater than 1, and applies to the memory 5 an order 13 as soon as this mean value corresponds to an actual value lower than 60/150th of a second or higher than 60/45th of a second; the discriminator 6 also permanently applies on the channel 14 a signal representing the value of each period $p_i$ which it measures.

Alternately, or simultaneously, a discriminator 6,7 or 8 may be designed to detect on the read-out signal 1b supplied by the reader 1 a peak corresponding to the emission of an electric pulse coming from a cardiac stimulation apparatus worn by the patient; the discriminator 6,7 or 8 is then arranged to give an order 13 to the memory 3,4 or 5 with which it is associated, in response to the detection of said peak.

Alternately or simultaneously, a discriminator 6,7 or 8 may be designed to compare the shape of the patterns of the signal 1b with a reference shape, corresponding to a normal electrocardiogram. This discriminator is arranged to apply to the memory 3,4 or 5 associated therewith a signal 13 when the variation between the shape of a pattern of the signal 1b and the reference shape is greater than a predetermined value. This variation may for example be assessed quantitatively by measuring the area defined between the measured and reference tracings of the patterns. It is possible to limit this recognition of shape and this measurement of variation by the discriminator to the wave QRS and/or to wave P and/or to wave T of the pattern.

Of course, each discriminator 6,7 or 8 may be provided both with means for recognizing shape and with means for measuring the periods and comparing these periods in actual or mean value, with a reference value; it is thus possible to select a pathological complex characterised both by an abnormal value of the period and by an abnormal shape of the cycle, for example a widening of the signal QRS.

The display apparatus 12 is arranged so that the recording of each sequence remains stable on the screen and disappears only upon the appearance on the signal 1b of a new pathological occurrence—or complex—of the same type, to be replaced by the corresponding new sequence. Centering means are provided so that the wave QRS of the pattern presenting an abnormality is located at the same place on the screen.

The operator may, of course, stop the advance of the magnetic tape in the reader 1 at any moment, in order to examine a sequence more fully and/or to record it on paper.

According to an embodiment of the invention, a discriminator, for example discriminator 6, is designed to supply an order 15 to the motor 1a to stop when it detects a strongly pathological complex such as a highly abnormal widening of the signal QRS or an abnormally short period $p_i$ or a succession of very short periods $p_i$ (salvo of extrasystoles). The operator may at this moment give—or not give—a computer 16 exploiting the signal 1b, an enabling order 17 allowing the computer 16 to take into account—or not to take into account—this pathological occurrence for a statistical processing such as a histogram.

Instead of a display apparatus having a plurality of channels, an apparatus having only one channel may be used, provided with a suitable device for allowing the display of the contents of the memories 3,4,5 in different screen locations; for example, the different contents may be successively received on the display apparatus and a continuous signal of different level may be added to the signal coming from each memory 3,4,5.

What is claimed is:

1. A method of processing and displaying an electrocardiogram signal that has been recorded at a first speed, comprising the steps of:
   reading said recorded signal at a speed greater than the first speed of recording;
   selectively and simultaneously detecting the occurrence of a plurality of types of pathological complexes from the read signal; and
   simultaneously displaying a signal sequence of said read signal for each detected pathological complex at respective different ones of a plurality of distinct display locations.

2. The method of claim 1, wherein the step of selectively and simultaneously detecting selectively detects the occurrence of a particular type of pathological complex by measuring each period of the read signal and comparing each said measured period with a reference value.

3. The method of claim 1, wherein the step of selectively and simultaneously detecting selectively detects the occurrence of a particular type of pathological complex by measuring each period of the read signal and determining whether each measured period is included in a range between two reference values.

4. The method of claim 1, wherein the step of selectively and simultaneously detecting selectively detects the occurrence of a particular type of pathological complex by measuring each period of the read signal, calculating the difference between each measured period and the immediately preceding period and comparing each difference with a reference value.

5. The method of claim 1, wherein the step of selectively and simultaneously detecting selectively detects the occurrence of a particular type of pathological complex by measuring each period of the read signal, calculating a mean value for each n consecutive measured periods, n being an integer greater than 1, and comparing each mean value with a reference value.

6. The method of claim 1, wherein the step of selectively and simultaneously detecting selectively detects the occurrence of a particular type of pathological complex by measuring each period of the read signal, calculating a mean value for each n consecutive measured periods, n being an integer greater than 1, and determining whether each mean value is included in a range between two reference values.

7. The method of claim 1, wherein the step of selectively and simultaneously detecting selectively detects the occurrence of a particular type of pathological complex by measuring each period of the read signal, comparing each measured period with a reference value and detecting each series of p consecutive cycles of the read signal in which the measured periods are one of lower and higher than said reference value, p being an integer greater than 1.

8. The method of claim 1, wherein the step of selectively and simultaneously detecting selectively detects the occurrence of a particular type of pathological complex by comparing the shape of each cycle of the read signal with a reference shape.

9. Apparatus for processing and displaying an electrocardiogram signal that has been recorded at a first speed on a recording medium, comprising:

reading means for reading said recorded signal at a speed greater than the first speed of recording;

delay means for delaying said read signal;

a plurality of memory means, each receiving the delayed signal from said delay means;

a plurality of discriminator means, each adapted to detect the occurrence of a type of pathological complex in the read signal from said reading means and each discriminator means controlling a respective one of said memory means to record a signal sequence of the delayed signal corresponding to a respective type of pathological complex upon the detection of said respective type of pathological complex; and display means including a plurality of distinct display locations, each adapted to display a respective signal sequence recorded by a respective one of said memory means, whereby each display location is associated with a particular type of pathological complex.

10. Apparatus according to claim 9; wherein said recording medium is a magnetic tape.

* * * * *